United States Patent
Liu et al.

(10) Patent No.: US 9,980,657 B2
(45) Date of Patent: May 29, 2018

(54) DATA RECOVERY FOR OPTICAL HEART RATE SENSORS

(71) Applicant: MICROSOFT TECHNOLOGY LICENSING, LLC, Redmond, WA (US)

(72) Inventors: Zongyi Liu, Issaquah, WA (US); Haithem Albadawi, Redmond, WA (US); Qing Xie, Sammamish, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 311 days.

(21) Appl. No.: 14/291,613

(22) Filed: May 30, 2014

(65) Prior Publication Data

US 2015/0342479 A1    Dec. 3, 2015

(51) Int. Cl.
*A61B 5/024* (2006.01)
*A61B 5/0245* (2006.01)
*A61B 5/00* (2006.01)

(52) U.S. Cl.
CPC ........ *A61B 5/02427* (2013.01); *A61B 5/0245* (2013.01); *A61B 5/02416* (2013.01); *A61B 5/02438* (2013.01); *A61B 5/721* (2013.01)

(58) Field of Classification Search
CPC . A61B 5/0059; A61B 5/02416; A61B 5/0261; A61B 5/02154; A61B 5/02427;

(Continued)

(56) References Cited

U.S. PATENT DOCUMENTS 4,420,000 A * 12/1983 Bailey .................... A61B 5/024
                                                          600/519
4,938,228 A * 7/1990 Righter ................ A61B 5/0245
                                                          600/503

(Continued)

FOREIGN PATENT DOCUMENTS

WO    2013038296 A1    3/2013

OTHER PUBLICATIONS

Fingas, Jon, "TomTom's new GPS watches track your heart rate without a chest strap (update: US pricing)", http://www.engadget.com/2014/04/03/tomtom-cardio-gps-watches/, Apr. 3, 2014, 10 pages.

(Continued)

*Primary Examiner* — Amelie R Gillman
*Assistant Examiner* — Carolyn Pehlke
(74) *Attorney, Agent, or Firm* — Alleman Hall Creasman & Tuttle LLP (57) ABSTRACT

An optical heart rate sensor stores data indicating the timing of heart beats in a first-in-first-out rolling buffer. During a first condition, new data is added to the rolling buffer and adjusted such that a duration preceding a newly detected heart beat is closer to an average duration between each pair of consecutive heart beats stored in the rolling buffer if the duration preceding the newly detected heart beat differs from the average duration by more than a duration threshold. The rolling buffer is cleared when a number of data adjustments over a predetermined time period exceeds a counting threshold. The rolling buffer is then repopulated such that the duration between each pair of consecutive heart beats is equal to a most recent duration between consecutive heart beats that did not differ from the average duration by more than the duration threshold.

19 Claims, 8 Drawing Sheets

(58) Field of Classification Search
CPC ..... A61B 5/0245; A61B 5/721; G06T 7/0012; G06F 17/17; G06F 17/18
USPC ............... 600/479, 508, 509, 473, 476, 520; 382/128–132; 702/189–199
See application file for complete search history.

(56) References Cited

U.S. PATENT DOCUMENTS

| | | | |
|---|---|---|---|
| 6,905,470 | B2 | 6/2005 | Lee et al. |
| 7,043,294 | B1 | 5/2006 | Paris |
| 8,032,206 | B1 | 10/2011 | Farazi et al. |
| 8,452,404 | B1 | 5/2013 | Fischell et al. |
| 2002/0038094 | A1 | 3/2002 | Gorman |
| 2004/0059234 | A1 | 3/2004 | Martin et al. |
| 2005/0206876 | A1 | 9/2005 | Reeves et al. |
| 2007/0118043 | A1 | 5/2007 | Oliver et al. |
| 2007/0208263 | A1 | 9/2007 | John et al. |
| 2009/0112111 | A1 | 4/2009 | Shimizu et al. |
| 2011/0098583 | A1 | 4/2011 | Pandia et al. |
| 2012/0078120 | A1 | 3/2012 | Ahmed et al. |
| 2014/0073964 | A1* | 3/2014 | Rodriguez-Llorente A61B 5/7207 600/479 |
| 2014/0275854 | A1* | 9/2014 | Venkatraman ......... A61B 5/721 600/301 |

OTHER PUBLICATIONS

Goode, Lauren, "Samsung's New Gear Fit Needs to Work on the "Fit" Part", http://recode.net/2014/04/08/samsungs-new-gear-fit-needs-to-work-on-the-fit-part/, Apr. 8, 2014, 10 pages.
"Samsung Gear Fit, Gear 2 and Gear 2 Neo go on sale worldwide", NDTV Gadgets, http://gadgets.ndtv.com/others/news/samsung-gear-fit-gear-2-and-gear-2-neo-go-on-sale-worldwide-507220, Apr. 11, 2014, 3 pages.
Poeter, Damon, "Meet Simband, Samsung's Next-Gen Health Tracker", http://www.pcmag.com/article2/0,2817,2458663,00.asp, May 28, 2014, 5 pages.
ISA European Patent Office, International Search Report and Written Opinion Issued in Application No. PCT/US2015/032336, dated Sep. 1, 2015, WIPO, 9 Pages.

* cited by examiner

| HEART BEAT # | 1 | 2 | 3 | 4 | 5 | 6 | 7 | 8 | 9 | 10 | NEW |
|---|---|---|---|---|---|---|---|---|---|---|---|
| PULSES SINCE PRIOR BEAT | 60 | 60 | 60 | 60 | 60 | 60 | 60 | 60 | 60 | 60 | 55 |
| HEART RATE | 60 | 60 | 60 | 60 | 60 | 60 | 60 | 60 | 60 | 60 | 65.5 |

BUFFER AVERAGE HEART RATE = 60 BPM    THRESHOLD +/- 8.4 BPM

420

| HEART BEAT # | 1 | 2 | 3 | 4 | 5 | 6 | 7 | 8 | 9 | 10 | NEW |
|---|---|---|---|---|---|---|---|---|---|---|---|
| PULSES SINCE PRIOR BEAT | 60 | 60 | 60 | 60 | 60 | 60 | 60 | 60 | 60 | 55 | 45 |
| HEART RATE | 60 | 60 | 60 | 60 | 60 | 60 | 60 | 60 | 60 | 65.5 | 80 |

BUFFER AVERAGE = 60.5 BPM    THRESHOLD +/- 8.4 BPM

430

| HEART BEAT # | 1 | 2 | 3 | 4 | 5 | 6 | 7 | 8 | 9 | 10 | NEW |
|---|---|---|---|---|---|---|---|---|---|---|---|
| PULSES SINCE PRIOR BEAT | 60 | 60 | 60 | 60 | 60 | 60 | 60 | 60 | 55 | 52 | 71 |
| HEART RATE | 60 | 60 | 60 | 60 | 60 | 60 | 60 | 60 | 65.5 | 68.9 | 51 |

BUFFER AVERAGE = 61.5 BPM    THRESHOLD +/- 8.5 BPM

440

| HEART BEAT # | 1 | 2 | 3 | 4 | 5 | 6 | 7 | 8 | 9 | 10 | NEW |
|---|---|---|---|---|---|---|---|---|---|---|---|
| PULSES SINCE PRIOR BEAT | 60 | 55 | 52 | 68 | 60 | 53 | 50 | 53 | 49 | 48 | 45 |
| HEART RATE | 60 | 65.5 | 69 | 53 | 60 | 68 | 72 | 68 | 73.5 | 75 | 80 |

BUFFER AVERAGE = 66.4 BPM    THRESHOLD +/- 9.2 BPM

450

| HEART BEAT # | 1 | 2 | 3 | 4 | 5 | 6 | 7 | 8 | 9 | 10 |
|---|---|---|---|---|---|---|---|---|---|---|
| PULSES SINCE PRIOR BEAT | 53 | 53 | 53 | 53 | 53 | 53 | 53 | 53 | 53 | 53 |
| HEART RATE | 68 | 68 | 68 | 68 | 68 | 68 | 68 | 68 | 68 | 68 |

BUFFER AVERAGE = 68 BPM    THRESHOLD +/- 9.4 BPM

DATA RECOVERY FOR OPTICAL HEART RATE SENSORS

BACKGROUND

Monitoring heart rate levels provides useful health information, such as an overall fitness level. Optical heart rate sensors provide a non-invasive means of determining heart rate levels. An optical heart rate sensor may be incorporated into a wearable device.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

An optical heart rate sensor stores data indicating the timing of heart beats in a first-in-first-out rolling buffer. During a first condition, new data is added to the rolling buffer and adjusted such that a duration preceding a newly detected heart beat is closer to an average duration between each pair of consecutive heart beats stored in the rolling buffer if the duration preceding the newly detected heart beat differs from the average duration by more than a duration threshold. The rolling buffer is cleared when a number of data adjustments over a predetermined time period exceeds a counting threshold. The rolling buffer is then repopulated such that the duration between each pair of consecutive heart beats is equal to a most recent duration between consecutive heart beats that did not differ from the average duration by more than the duration threshold. In this way, the optical heart rate sensor may robustly provide accurate data and rapidly recover when errors or poor quality data is indicated.

DETAILED DESCRIPTION

The present disclosure is directed to monitoring the signal quality of an optical heart rate sensor, and in particular, to increasing the robustness of an optical heart rate sensor by providing methods for recovering data quickly upon detection of errors or data of poor quality. For example, different types of errors may be detected by comparing current heart rate data with previous heart rate data. While described herein in the context of a wearable computing device, it is to be understood that monitoring the signal quality of an optical heart rate sensor, as described herein, may be used in numerous different applications, and with various different types of sensory-and-logic systems.

Incorporating an optical heart rate sensor into a wearable computing device allows a user to constantly monitor health factors, such as heart rate, calories burned, response to exertion exercises, heart rate variability, etc. However, the signal from the optical sensor may degrade in quality with increased motion, as user motion may change the optical properties of the skin, tissues, and blood vessels beneath the optical sensor. This may result in the optical heart rate sensor outputting inaccurate data. Further, recovering accurate measurements following error detection may be problematic, and may be exacerbated while the optical heart rate sensor is in use. Optical heart rate sensors are prone to outputting high heart rates during certain movements. For example, if a user is typing or playing piano while wearing the optical heart rate sensor on their wrist, the repetitive motions may mimic heart beats, and result in inaccurate measurements. Further, if the motion-level of the user is changing during a resetting of the sensor following an error, the recovery rate of accurate heart rate data may be slow.

In order to address these problems, the optical heart rate sensor may be configured to discern different types of errors by comparing current heart rate data with recent, previously detected data. This may include determining whether the optical sensor is stable or unstable. If the optical sensor is stable, and a number of outlier heart rates within a time period is small, the outlier heart rates may be adjusted based on recent data. If the optical sensor is stable, and the number of outlier heart rates within a time period is large, the recent, previously detected data may be reset based on the most recent unadjusted heart rates. The reset may be effected by recognizing that the previously detected data is no longer an accurate representation or indication of current heart rate given that the number of outliers is large. Newly detected heart rates may then be compared to the reset data, i.e., one or more detected data that more accurately reflects heart rate data in view of the outlier data. If the optical sensor is not stable, for example if the light intensity detected by the optical sensor is changing rapidly, the recent, previously detected data may be cleared and repopulated after determining an average heart rate over a time period encompassing multiple heart beats. Newly detected beats may then be compared to the repopulated data. In this way, the optical heart rate sensor may robustly provide accurate data and rapidly recover when errors or poor quality data is indicated.

Figures 1A, 1B:
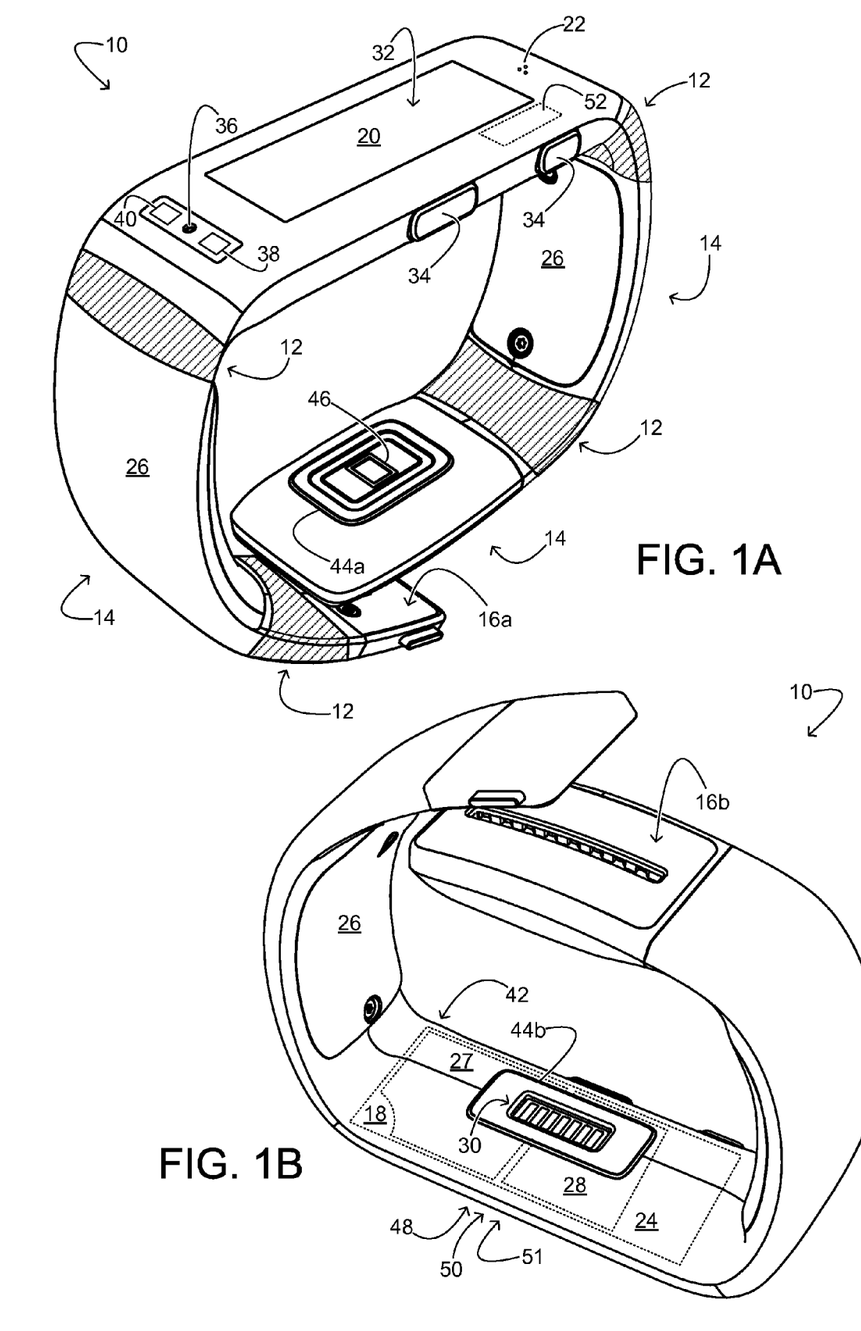
FIGS. 1A and 1B show a wearable electronic device.

FIGS. 1A and 1B show aspects of an example sensory-and-logic system in the form of a wearable electronic device 10 that includes an optical heart rate sensor 46. The illustrated device is band-shaped, with at least four flexion regions 12 linking less flexible regions 14. The flexion regions may be elastomeric in some examples. Fastening componentry 16A and 16B is arranged at both ends of the device. The flexion regions and fastening componentry enable the device to be closed into a loop and to be worn on a user's wrist. In other implementations, wearable electronic devices of a more elongate band shape may be worn around the user's bicep, waist, chest, ankle, leg, head, or other body part. The device, for example, may take the form of eye glasses, a head band, an arm-band, an ankle band, a chest strap, or an implantable device to be implanted in tissue.

Wearable electronic device 10 includes various functional components integrated into regions 14. In particular, the electronic device includes a compute system 18, display 20, loudspeaker 22, communication suite 24, and various sensors, including optical heart rate sensor 46. These components draw power from one or more energy-storage cells 26. A battery—e.g., a lithium ion battery—is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable electronic device may include electro-mechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable electronic device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. Aspects of the compute system are described in further detail with reference to FIGS. 2 and 8.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable electronic device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable electronic device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, etc.

FIGS. 1A and 1B show various other sensors of wearable electronic device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin. Compute system 18 may use such input to assess whether or not the device is being worn, for instance. In some implementations, the sensory function may be used to determine how tightly the wearable electronic device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44B in the illustrated configuration is the optical heart rate sensor 46. The optical heart rate sensor may include an optical source and matched optical sensor to detect blood flow through the capillaries in the skin and thereby provide a measurement of the wearer's heart rate, blood oxygen level, blood glucose level, or other biomarkers with optical properties. Further details regarding the optical heart rate sensor, optical source, and optical sensor are provided with reference to FIG. 2.

Wearable electronic device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer and/or calorie-counting function, for example. Data from the accelerometer and gyroscope may be combined with geomagnetic data from the magnetometer to further define the inertial and rotational data in terms of geographic orientation. The wearable electronic device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable electronic device, and only non-personal, summary data transmitted to the remote system.

Figure 2:
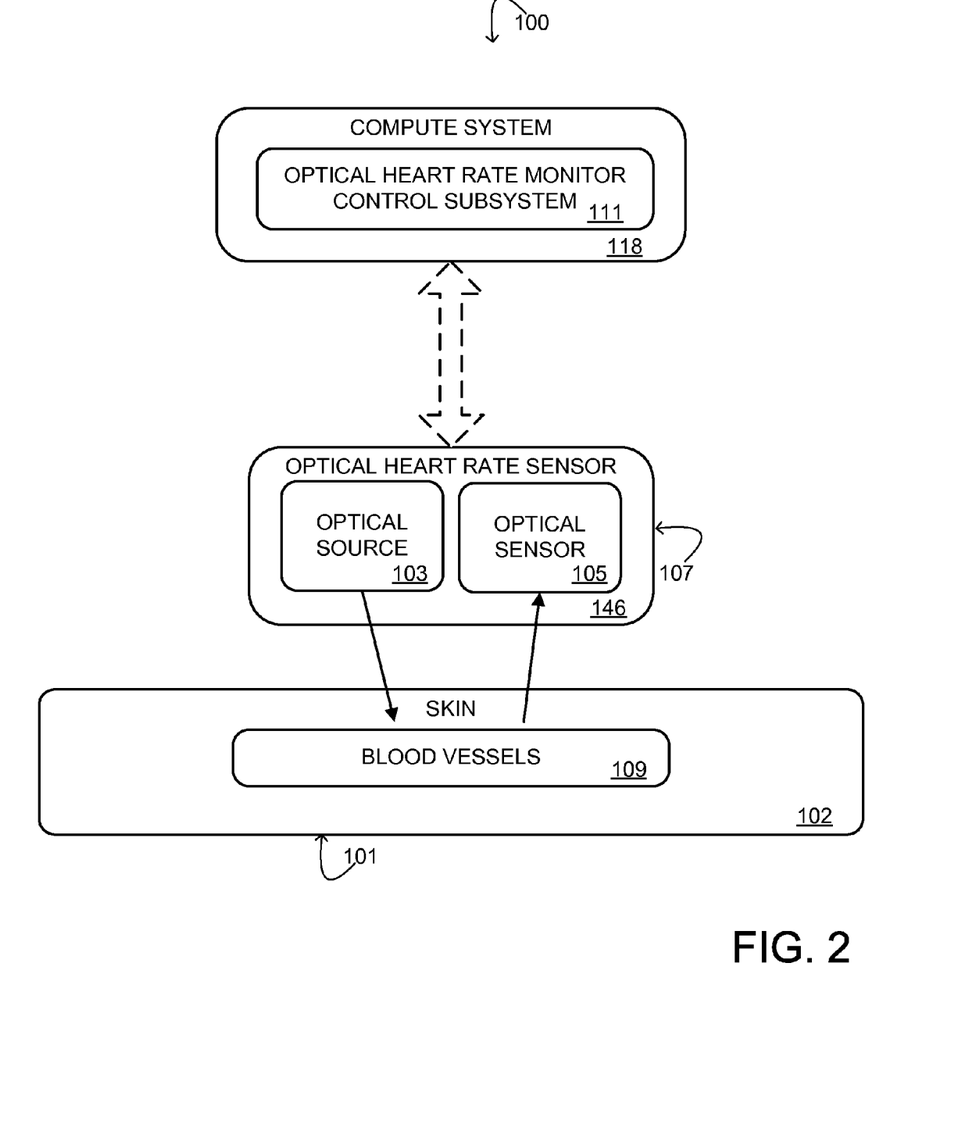
FIG. 2 schematically shows an example optical heart rate sensor.

FIG. 2 shows a schematic depiction of a sensory-and-logic system 100 coupled to the wrist of a user 101 so that an optical heart rate sensor 146 is adjacent to the skin 102 of user 101. Optical heart rate sensor 146 comprises an optical source 103 configured to illuminate one or more blood vessels through the skin of the user, and an optical sensor 105, configured to measure reflected illumination from the blood vessels. Optical source 103 may comprise one or more LED emitters, for example, while optical sensor 105 may comprise one or more photodiodes matched to detect light at frequencies that are based on the frequencies of light output by the optical source. Optical heart rate sensor 146 may be coupled within a housing 107 configured to promote contact between sensor 146 and skin 102, and further configured to block, filter, or otherwise limit ambient light from reaching the optical sensor. In this way, the majority of light reaching optical sensor 105 may be light originating from optical source 103 that has reflected off of blood vessels 109 beneath skin 102. As an example, FIG. 1A shows a wearable electronic device 10 that is configured to position optical heart rate sensor 46 such that its optical source may illuminate capillaries located beneath the skin of the user's forearm while the wearable electronic device is worn by the user. In other configurations, an optical heart rate sensor may be positioned within a wearable electronic device such that an optical source illuminates a radial artery through the skin of the user while the wearable electronic device is worn by the user. Alternatively, an optical heart rate sensor and its associated compute system may be housed separately and configured to communicate via a communication suite. For example, an optical heart rate sensor may be included in a head set and configured to illuminate capillaries located in the user's ear lobe while the head set is worn by the user. An optical sensor may be configured to sense light reflected off of blood vessels located beneath the skin of the user (e.g., wrist worn), or the optical sensor may be configured to sense light transmitted through blood vessels located beneath the skin of the user (e.g., ear worn).

Compute system 118 may comprise optical heart rate sensor control subsystem 111. Optical heart rate sensor control subsystem 111 may provide control signals to optical source 103 and optical sensor 105. Optical heart rate sensor control subsystem 111 may receive raw signals from optical sensor 105, and may further process the raw signals to determine heart rate, caloric expenditures, and other physical measures. Processed signals may be stored and output via compute system 118. Control signals sent to optical source 103 and optical sensor 105 may be based on signals received from optical sensor 105, one or more motion sensors, ambient light sensors, information stored in compute system 118, input signals, etc. Recent data received from optical sensor 105 may be stored in a first-in, first-out rolling buffer. Rolling buffers may also be maintained for recent data received from other sensors (e.g. motion sensors), for processed data (e.g. recent heart rates), and other measured or calculated data. Control signals provided to optical source 103 and optical sensor 105 may be based on the data stored in the rolling buffers.

Signals received from motion sensors and ambient light sensors may be used to filter raw data output from optical sensor 105 prior to determining heart rates. Further, optical source 103 may be operated in a pulsed-on mode, as opposed to a continuously-on mode. In this way, if optical sensor 105 is operated in a continuously-on mode while optical source 103 is pulsed on and off, optical sensor 105 will detect ambient light when optical source is off. The ambient light detected may be subtracted from, or otherwise used to smooth the raw signal from optical sensor 105.

Figure 3A:
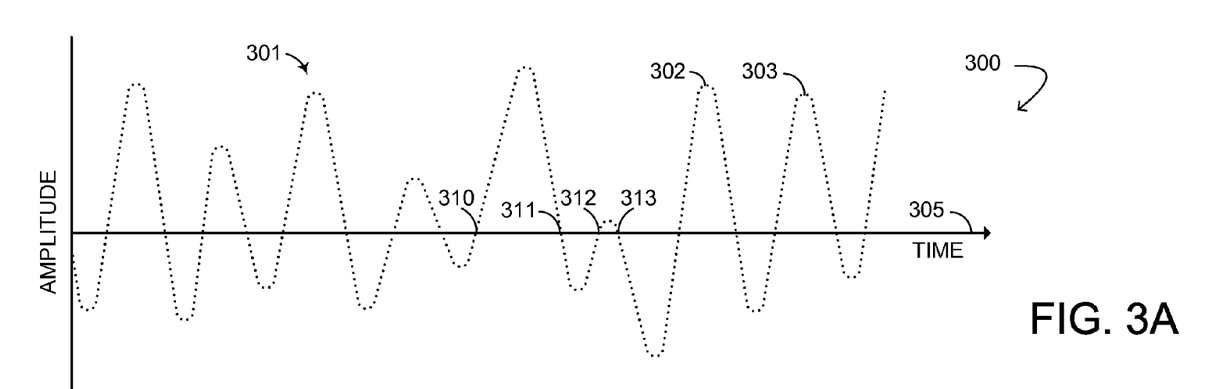
FIGS. 3A and 3B show example data traces output by an optical heart rate sensor.

FIG. 3A shows an example chart 300 of data that may be output from optical sensor 105. Chart 300 includes plot 301, indicating the amplitude of a signal received from optical sensor 105 over time. The movement of blood through the blood vessels causes the blood vessels to expand and contract, thus causing a change in the optical properties of the user's skin. The color of blood also changes across the heart beat cycle, as newly pumped blood contains more oxygen, and thus has a different absorption spectrum than blood exiting the local blood vessels. The repetitive nature of the heart beat yields a periodic plot when illuminated by an optical source. Each successive heart beat yields an amplitude peak, such as amplitude peaks 302 and 303. The length of time between peaks may thus be used to determine a heart rate. Raw data may be filtered and processed to smooth the data, and a threshold amplitude may be determined to eliminate the selection of false peaks.

As the amplitude of the peaks may change from beat to beat, heart rate may be calculated by other methods, alternatively or in addition to peak detection. For example, a zero-axis 305 may be determined and applied to the data. Each heart beat thus comprises two zero-crossing events, a negative-to-positive zero-crossing event, such as zero-crossing events 310 and 312, and a positive-to-negative zero-crossing event, such as zero-crossing events 311 and 313. As such, the length of time between alternating zero-crossing events, such as zero-crossing events 310 and 312 or 311 and 313, may be used to determine a heart rate.

The individual data points shown in plot 301 correspond to light pulsations emitted from optical source 103 as subsequently detected by optical sensor 105. If optical source 103 is configured to emit light at a predetermined pulsation frequency, the timing of each heart beat and thus the duration between heart beats may be recorded based on specific light pulsations, as opposed to being recorded based on absolute time. For example if optical source 103 has a pulsation frequency of 3600 pulses/minute, and the duration between alternating zero-crossing events is 60 pulses, a heart rate between adjacent heart beats would be calculated as 60 beats per minute.

Figure 3B:
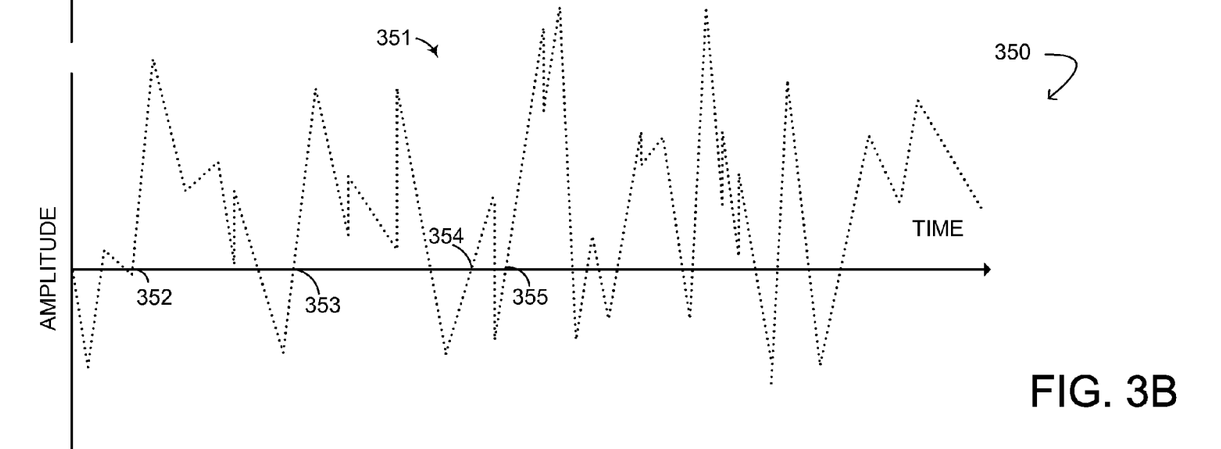

The example data shown in chart 300 has a high signal to noise ratio that provides easily-discernible peaks and zero-crossing events. However, data output from optical sensor 105 may be more complex. FIG. 3B shows an example chart 350 of data that may be output from optical sensor 105. Chart 350 includes plot 351, indicating the amplitude of a signal received from optical sensor 105 over time. Plot 351 has a lower signal to noise ratio than does plot 301. Numerous factors may contribute to the addition of noise to the output of optical sensor 105. User motion may contribute to the moving of fluid through and near blood vessels that may not be discernible from blood flow driven by heart beats. If optical heart rate sensor housing 107 has poor contact with the skin of the user, the amount of ambient light reaching optical sensor 105 may change, increasing the signal-to-noise ratio. Similarly, if optical sensor 105 is seated improperly within optical heart rate sensor housing 107, signal-to-noise ratio may be increased over a properly seated optical sensor.

With a decreased signal to noise ratio, peaks and zero-crossing events may emerge that are due to user motion, or other factors, rather than user heart beats. As an example, user motion may give rise to erratic, high frequency signals that are outside the range of normal heart rates. For example, multiple zero-crossing events, such as zero-crossing events 352 and 353, or zero-crossing events 354 and 355 may emerge over the course of a single heart beat due to increased user motion. Based on the recent history of user heart rates, and/or signals received from motion sensors, the higher frequency events may be filtered or ignored. However, consistently poor quality data may be indicative of an underlying sensor problem.

In order to track and evaluate the quality of data from the optical sensor, a first-in-first-out rolling buffer of heart rates may be stored in the data-storage machine. By comparing newly detected data to the recent data stored in the rolling buffer, the accuracy of each newly detected heart beat may be determined. Further, it may be possible to discern different types of sensor errors, which may allow for proper recovery methods to be selected based on the type of error, so that accurate heart rate measurements may be output quickly following a sensor error.

Figure 4:
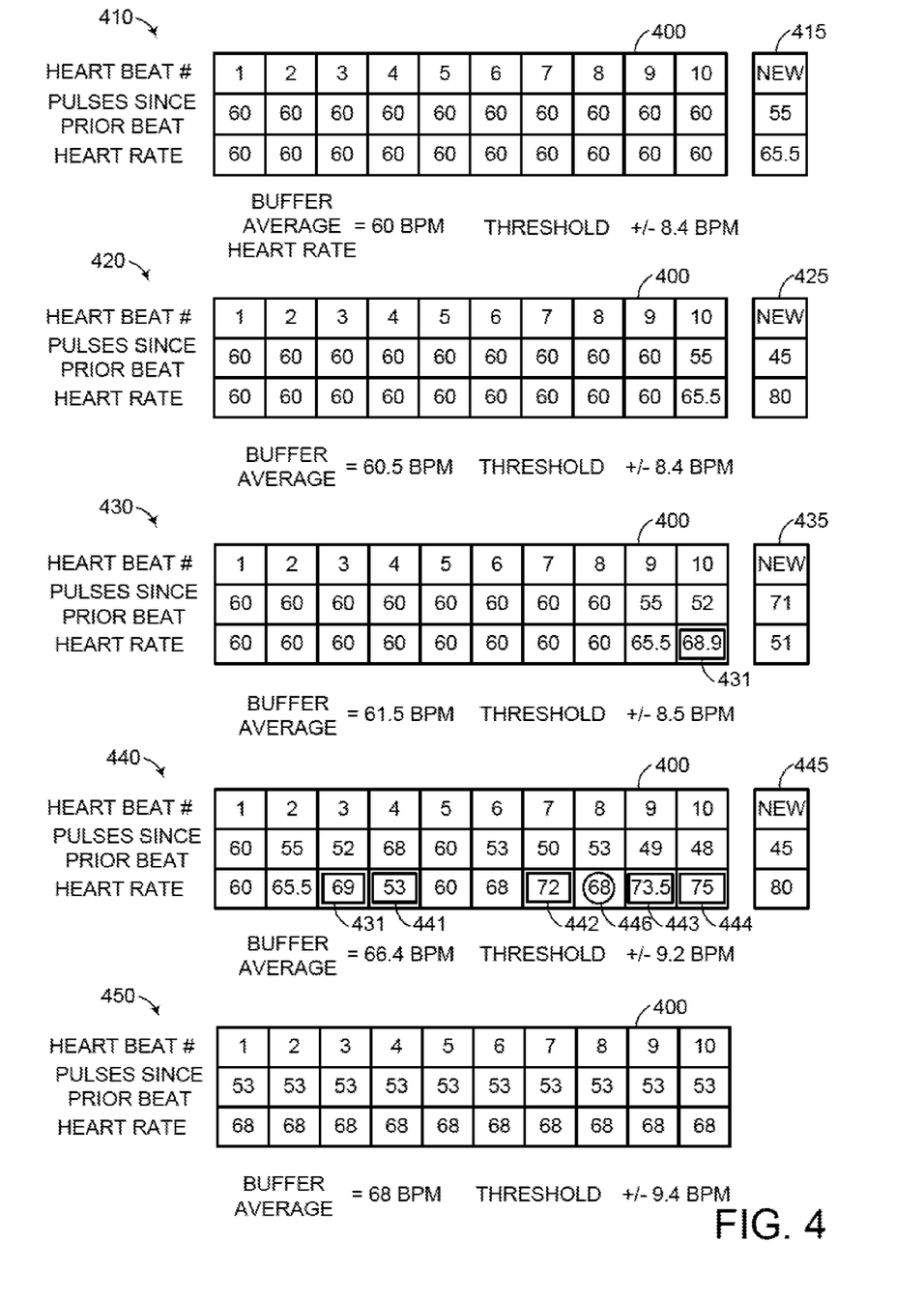
FIG. 4 shows example data that may be stored in a rolling heart rate buffer of the optical heart rate sensor.

FIG. 4 shows an example of an initial rolling heart rate buffer 400 for the optical heart rate sensor described herein and with regard to FIG. 2. For simplicity, 10 recent heart rates are shown, though the rolling buffer may comprise a smaller or larger number of recent heart rates, for example, 36 recent heart rates. When the optical heart rate sensor is activated or reset, initial rolling heart rate buffer is populated with data indicative of a constant, default heart rate. In this example, the default heart rate is set at 60 beats per minute (bpm), as shown at 410. The default heart rate may be a predetermined value, a value based on a most recent heart rate, a value based on a selected application, a value based on an amount of motion determined by one or more motion sensors, etc.

In this example, the pulsation frequency of the optical sensor is fixed at 3600 pulses/minute. Thus, for a constant heart rate of 60 bpm, each heart beat is given a value set 60 pulsations following the previously detected beat in the rolling buffer, as indicated in the "pulses since prior beat" row of rolling buffer 400. In this example, the pulsation number for each detected heart beat is representative of a zero-crossing event of a processed signal from optical sensor 105. In other examples, the pulsation number may be representative of a detected peak, or other singular data point indicative of a detected heart beat. The buffer at 410 has an inherent average heart rate of 60 bpm.

The average heart rate for the buffer may be used to smooth data for newly detected heart rates, as it may be assumed that the users' heart rate can only change a certain amount over a short time period. In this way, newly detected heart beats that are significantly slower or faster than the buffer average may be adjusted to be closer to the buffer average. This will prevent inaccurate heart beats from being reported to the user, and/or used in downstream calculations, and limit their influence in smoothing subsequently detected heart beats. A threshold deviation from the buffer average may be set at a fixed number of beats per minute, as a percentage of the buffer average, or based on an algorithm, which may change based on other current or recent data, such as user motion or activity level. In this example, the buffer threshold is set at a value of (buffer average bpm +7)/8. For the buffer average of 60 bpm, the threshold is thus set at (60+7)/8, or +/−8.4 bpm. In some examples, the buffer average may be expressed as a duration of time elapsed between detected heart beats. In this example, the buffer average of 60 bpm is equivalent to a buffer average of 60 pulses, and thus an acceptable range (e.g., buffer average +/− a duration threshold) for a newly detected heart beat may be set between 52.6 pulses and 69.8 pulses (e.g., 3600/68.4=52.6, 3600/51.6=69.8).

For each newly detected heart beat, a heart rate is determined based on the timing of the newly detected heart beat, and the timing of the most recent previously detected heart beat. At 410, new heart beat 415 is detected 55 pulses following the previously detected heart beat (Heart beat #10 in rolling buffer 400). As such, the heart rate is determined to be 65.5 bpm. This is within the threshold of the buffer average (60 bpm+/−84 bpm). Accordingly, data indicating the timing of the newly detected heart beat is added to rolling buffer 400 without being adjusted, as shown at 420, while the oldest detected heart beat in the rolling buffer is removed.

At 420, the buffer average heart rate is now 60.5 bpm, and the threshold is set at +/−8.4 bpm. New heart beat 425 is detected 45 pulses following the previously detected heart beat, for a heart rate of 80 bpm. This heart rate is above the acceptable range of heart rates based on the buffer average and threshold (68.9 bpm). Accordingly, the timing data for the newly detected heart beat is adjusted so the newly determined heart rate is equal to the sum of the buffer average and the threshold. As shown at 430, the newly determined heart rate is given a value of 68.9 bpm, and thus the timing data is assigned a value of 57 pulsations following the previously detected heart beat. As indicated by the added rectangle surrounding the data point at 431, the adjustment may be flagged for follow up. If the number of adjusted heart beats over a predetermined time period exceeds a threshold, this may be indicative of a sensor or measurement error. The quantity of adjusted heartbeats over time may therefore be used to monitor signal quality from the optical sensor.

At 430, the buffer average heart rate is now 61.5 bpm, and the threshold is set at +/−8.5 bpm. New heart beat 435 is detected 71 pulses following the previously detected heart beat, for a heart rate of 51 bpm. This heart rate is below the acceptable range of heart rates based on the buffer average and threshold (53 bpm). Accordingly, the timing data for the newly detected heart beat is adjusted so that the newly determined heart rate is equal to the difference of the buffer average and the threshold. As shown at 440 (heart beat #4), the newly determined heart rate is given a value of 53 bpm, and thus the timing data is assigned to a value of 68 pulsations following the previously detected heart beat. The adjustment is flagged, as shown at 441.

At 440, rolling buffer 400 has advanced an additional 6 detected heart beats from 430. Numerous newly detected heart beats have been detected outside the acceptable range, as indicated at 442, 443, and 444. New heart beat 445 is detected 45 pulses following the previously detected heart beat, for a heart rate of 80 bpm, outside the acceptable range of heart rates based on the buffer average of 66.4 bpm and the threshold of +/−9.2 bpm. Including the newly detected heart beat, four of five recent heart beats have been adjusted, exceeding a predetermined threshold. In this scenario, the buffer may be considered "dirty" and may no longer accurately reflect the current heart rate of the user. At this point, the system may be recovered by clearing the buffer, and repopulating the buffer with data indicating a constant heart rate equal to the most recent unadjusted heart rate. In this example, at 440, the most recent unadjusted heart rate is 68 bpm, as indicated at 446. Similarly to the data shown at 410, each heart beat in the repopulated buffer at 450 may be given a value set 53 pulsations following the previously detected beat in the rolling buffer, indicating the heart rate of 68 bpm. The threshold may thus be set at (68+7)/8 or 9.4 bpm.

Newly detected heart beats may now be processed and smoothed based on the repopulated rolling buffer. However, in order to avoid storing inaccurate data in the rolling buffer, a predetermined number of newly detected heart beats may be ignored or discarded prior to adding new heart beats to the rolling buffer, as the most recent data implies that incoming data may be of low quality.

In addition to monitoring the overall quality of the signal output by the optical sensor, the stability of the sensor may also be monitored. For example, if the detected light intensity changes with a frequency above a threshold during a predetermined time period, it may be inferred that the sensor is unstable. Sensor instability may be caused by poor contact between the sensor and the user's skin, and/or to ambient light leaking through the optical heart rate sensor housing. This could be due to the wearable computing device moving about the wrist of the user, for example. In this scenario, the entire rolling buffer needs to be reset. However, this type of error indicates that the recent data is not reliable, and thus repopulating the buffer with a most recent unadjusted heart rate may not be sufficient to regain accurate heart rate detection.

Figure 5:
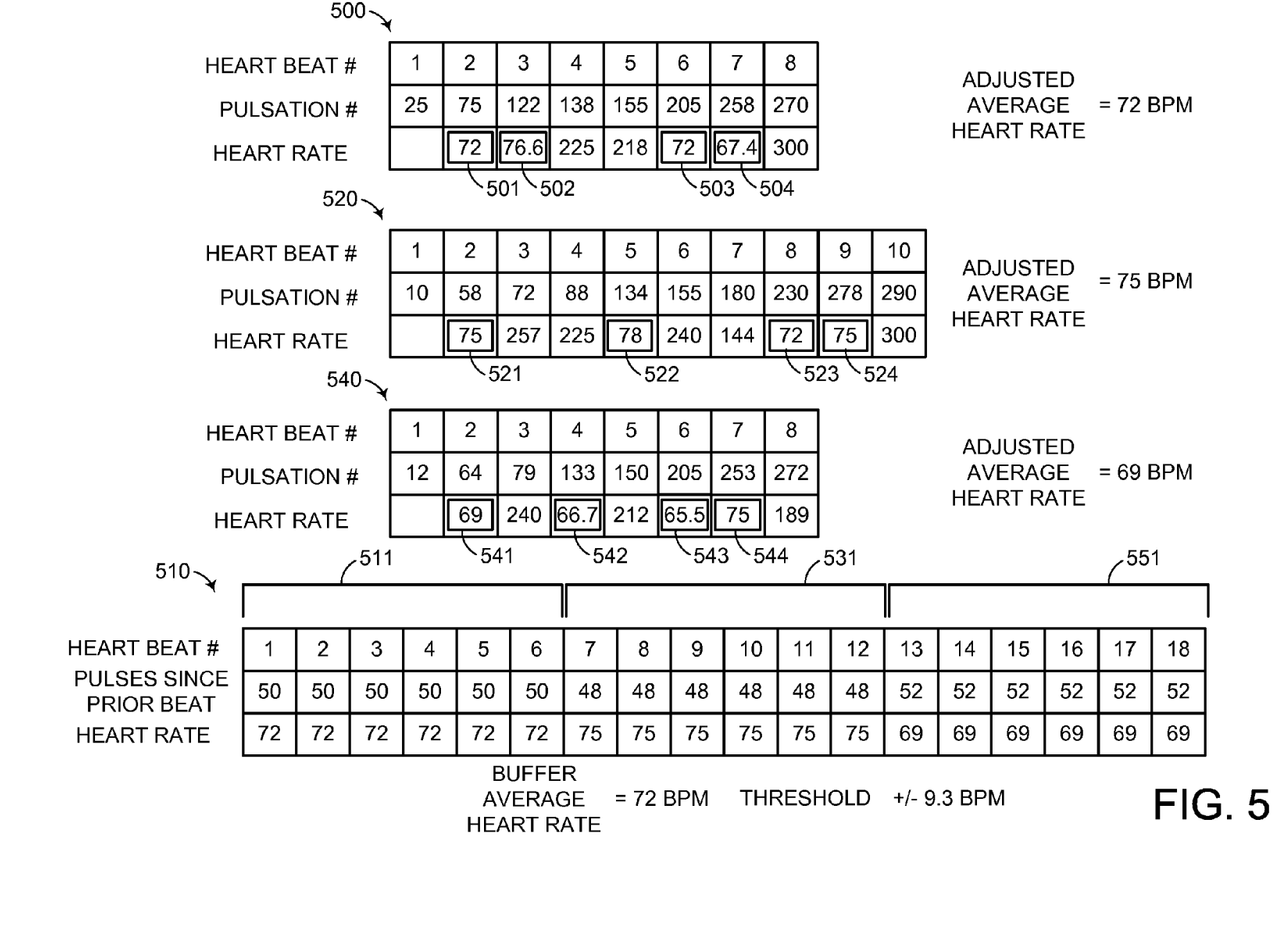
FIG. 5 shows example data that may be used to reset a rolling heart rate buffer of the optical heart rate sensor.

Rather, all internal buffers are cleared. This may include the rolling heart rate buffer, an internal motion buffer, an optical sensor data buffer, etc. Then, over a predetermined duration, all detected heart beats may be recorded, and an adjusted average heart rate determined. The adjusted average heart beat may comprise the average of determined heart rates that are below a threshold. High heart rates are more likely to be the product of signal noise, and thus lower determined heart rates are more likely to reflect the user's heart rate. The threshold may be predetermined, or based on the collected data. When the adjusted average heart rate is determined, a first segment of the rolling buffer may be repopulated with data indicating the adjusted average heart rate. The process may be repeated until the rolling buffer is filled. Similarly, the optical heart rate sensor may determine an adjusted rate or amount of motion over the predetermined time period, and a first segment of the motion buffer may be repopulated with the adjusted data. Data stored in the motion buffer may be used to filter the signal from the optical sensor prior to detecting heart beats, and thus the integrity of the motion buffer must be maintained to ensure accurate heart beat detection. FIG. 5 shows example data that may be generated during a rolling buffer resetting period. In this example, all detected heart beats are recorded over a five second period. At a pulsation frequency of 3600 pulses/min this will record heart rates over a 300 pulse window.

Table 500 shows example data taken over a first five second window. Eight heart beats are detected, but only the lowest four heart rates (501, 502, 503, and 504) are used to determine the adjusted heart rate average. The remaining, higher frequency heart rates are discarded. An adjusted average heart rate of 72 bpm is calculated, corresponding with an average of 50 pulses between heart beats. This adjusted average heart rate may then be used to repopulate a first segment of rolling buffer 510. In this example, rolling buffer 510 comprises 18 detected heart beats. First segment 511 is repopulated with 5 seconds (or 300 pulses) of data indicating the adjusted average heart rate of 72 bpm.

The process of detecting heart beats over a five second window and computing an adjusted average heart rate may then be repeated. Table 520 shows example data taken over a second five second (300 pulse) window. Here, ten heart beats are detected, and the lowest four heart rates (521, 522, 523, and 524) are used to calculate an adjusted average heart rate of 75 bpm, corresponding with an average of 48 pulses between heart beats. This second adjusted average may then be used to repopulate second segment 531 of rolling buffer 510. Second segment 531 is repopulated with 5 seconds (300 pulses) of data indicating the adjusted average heart rate of 75 bpm.

The process may be repeated until the rolling buffer is filled. Table 540 shows example data taken over a third five second window, with the lowest four heart rates (541, 542, 543, and 544) used to calculate an adjusted average heart rate of 69 bpm. This third adjusted average is then used to repopulate third segment 551 of rolling buffer 510 with five seconds of data indicating the adjusted average heart rate of 69 bpm.

The details of FIGS. 4 and 5 are provided only as examples. Initial seed values for the buffers, threshold magnitudes, the amounts to adjust violating readings before populating the buffer, the number/frequency of violations to trigger a buffer reset, the durations to consider when repopulating a reset buffer, or other particulars may be adjusted while remaining within the intended scope of this disclosure.

Figure 6:
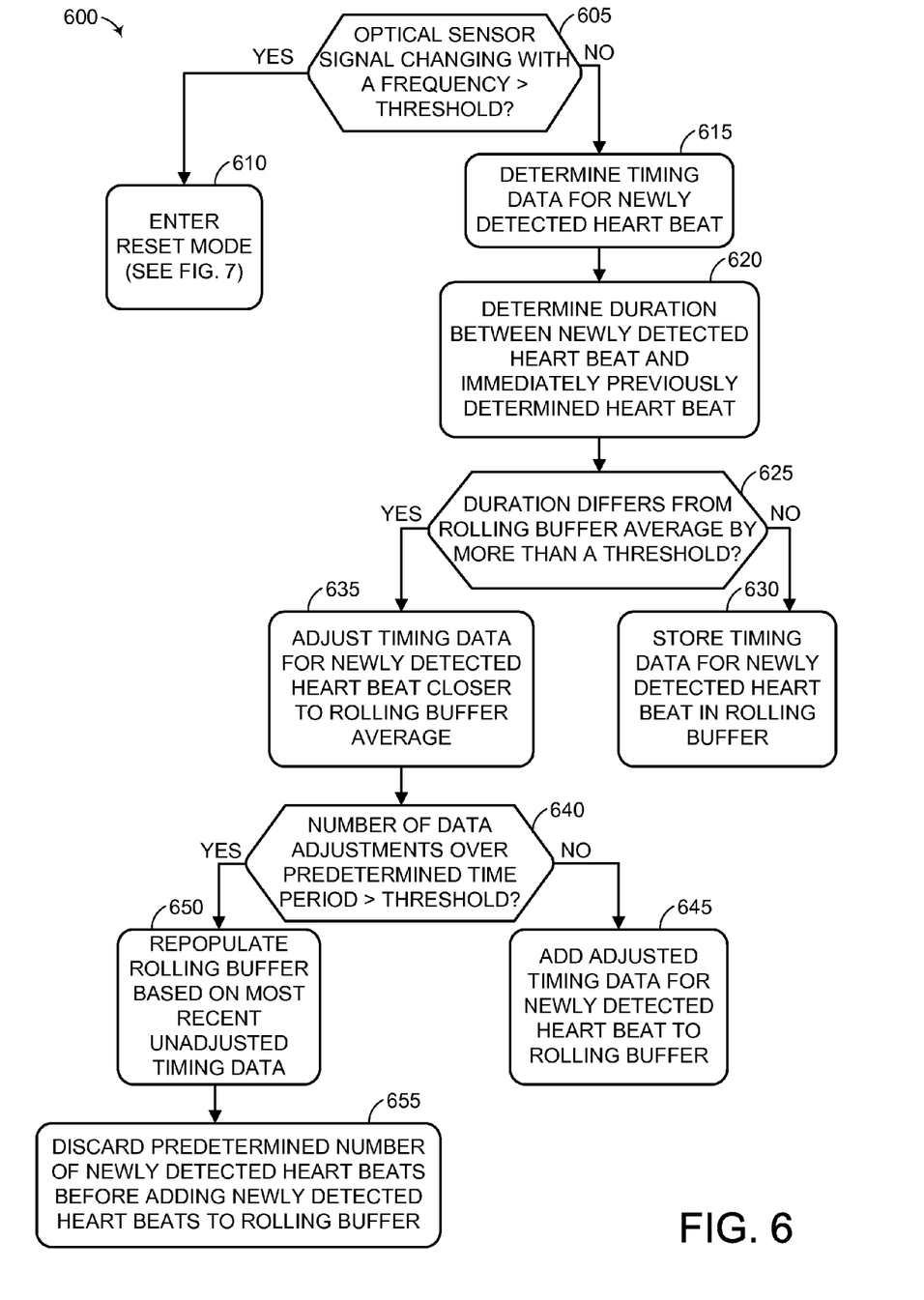
FIG. 6 shows an example method for monitoring signal quality of an optical heart rate sensor

The systems and techniques described herein may enable one or more methods of calculating a heart rate. FIG. 6 shows an example method 600 for recovering heart rate data for an optical heart rate sensor. Method 600 may begin at 605. At 605, method 600 may include determining whether an optical sensor signal is changing with a frequency greater than a threshold. If the optical sensor signal is changing with a frequency greater than a threshold, method 600 may proceed to 610. At 610, method 600 may include entering a reset mode. A subroutine for a reset mode is described with regards to FIG. 7.

If the optical sensor signal is not changing with a frequency greater than a threshold, method 600 may proceed to 615. At 615, method 600 may include determining timing data for a newly detected heart beat. As described with regards to FIGS. 3-5, data indicating a timing of a detected heart beat may comprise a timing of a zero-crossing event based on a received signal from the optical heart rate sensor. The timing of the zero-crossing event may be based on a timing of a light pulsation from an optical source of the optical heart rate sensor.

Continuing at 620, method 600 may include determining the duration between the newly detected heart beat and an immediately previously detected heart beat. The duration may be an absolute time period or based on a number of light pulses from the optical source. At 625, method 600 may include determining whether the duration between the newly detected heart beat and the immediately previously detected heart beat differs from the average duration between each pair of consecutive heart beats stored in a rolling buffer by more than a threshold. The rolling buffer may be a first-in-first-out rolling buffer. If the duration between the newly detected heart beat and an immediately previously detected heart beat does not differ from the average duration by more than the threshold, method 600 may proceed to 630. At 630, method 600 may include storing timing data for the newly detected heart beat in the rolling buffer.

If the duration between the newly detected heart beat and an immediately previously detected heart beat differs from the average duration by more than the threshold, method 600 may proceed to 635. At 635, method 600 may include adjusting the timing data for the newly detected heart beat to be closer to the average duration of the rolling buffer. For example, the duration between the newly detected heart beat and the immediately previously detected heart beat may be set equal to the sum of the rolling buffer average duration and the duration threshold if the duration between the newly detected heart beat and the immediately previously detected heart beat is greater than the sum of the average duration and the duration threshold. Further, the duration between the newly detected heart beat and the immediately previously detected heart rate may be set equal to the difference between the rolling buffer average duration and the duration threshold if the duration between the newly detected heart beat and the immediately previously detected heart beat is less than the difference of the average duration and the duration threshold. Alternatively, the duration may be shifted by a greater or lesser amount.

Continuing at 640, method 600 may include determining whether the number of data adjustments over a predetermined time period is greater than a counting threshold. If the number of data adjustments over the predetermined time period is not greater than the counting threshold, method 600 may proceed to 645, where the adjusted timing data for the newly detected heart beat is added to the rolling buffer.

If the number of data adjustments over the predetermined time period is greater than the counting threshold, method 600 may proceed to 650. At 650, method 600 may include clearing the rolling buffer, and repopulating the rolling buffer such that the duration between each pair of consecutive heart beats is equal to a most recent duration between consecutive heart beats that did not differ from the average duration by more than the duration threshold.

Continuing at 655, method 600 may include discarding a predetermined number of newly detected heart beats prior to adding newly detected heart beats to the rolling buffer. Each newly detected heart beat may be compared to the average duration of the repopulated rolling buffer and adjusted as described at 635.

Figure 7:
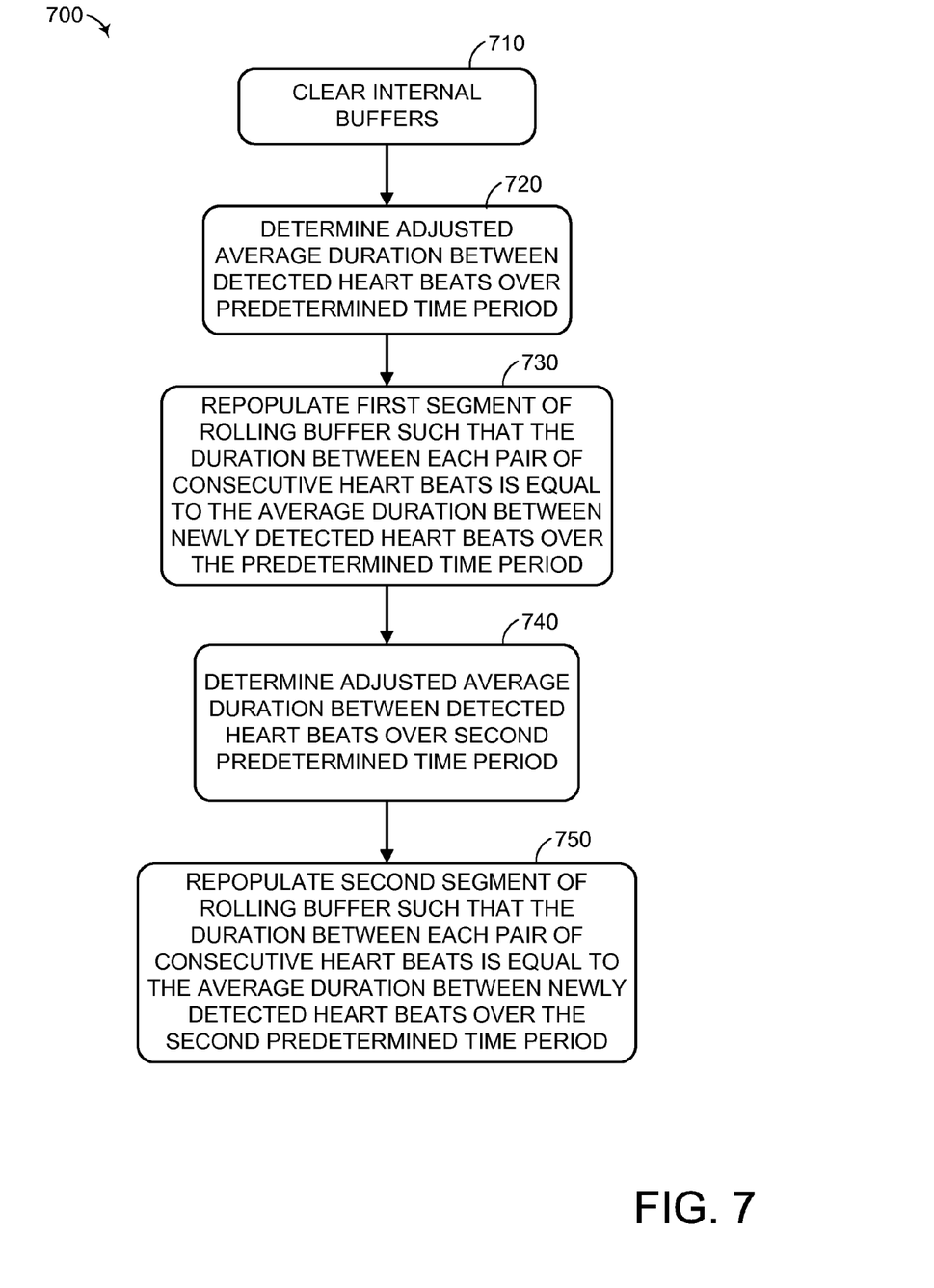
FIG. 7 shows an example method for resetting a rolling buffer of the optical heart rate sensor.

FIG. 7 shows an example method 700 for resetting a rolling buffer of an optical heart rate sensor. Method 700 may be run as a subroutine of method 600, or may be run as a standalone method when a signal from an optical sensor changes with a frequency above a threshold during a first predetermined time period.

Method 700 may begin at 710 by clearing the internal buffers of the optical heart rate sensor. This may include a rolling heart rate buffer, a motion buffer, an optical data buffer, or other buffer configured to store measured or calculated data or metadata. Continuing at 720, method 700 may include determining an adjusted average duration between detected heart beats over a second predetermined time period based on a measured intensity of light over the second predetermined time period. This may further include determining the duration between each pair of consecutive detected heart beats over the second predetermined time period, comparing each determined duration to a threshold, and determining the average duration between detected heart beats over the second predetermined time period based only on determined durations with values below the threshold. In this way, detected heart beats that are close together and likely to be derived from noise may be removed.

Continuing at 730, method 700 may include repopulating a first segment of the rolling buffer such that a duration between each pair of consecutive heart beats is equal to the average duration between newly detected heart beats over the second predetermined time period. While the rolling buffer is cleared and a first segment of the rolling buffer is repopulated, the rolling motion buffer may concurrently be cleared and a first segment of the rolling motion buffer may be repopulated based on signals received from one or more motion sensors over the first predetermined time period.

Continuing at 740, method 700 may include determining an adjusted average duration between detected heart beats over a third predetermined time period of equal duration to the second predetermined time period based on a measured intensity of light over the third predetermined time period. This may further include determining a duration between each pair of consecutive detected heart beats over the third predetermined time period, comparing each determined duration to a threshold, and determining the average duration based only on determined durations with values below the threshold.

Continuing at 750, method 700 may include repopulating a second segment of the rolling buffer such that a duration between each pair of consecutive heart beats is equal to the average duration between newly detected heart beats over the third predetermined time period.

The determination of an adjusted average duration between detected heart beats over a predetermined time period and the repopulation of segments of the rolling buffer based on the adjusted average duration may be repeated until the rolling buffer is filled. Then, for each newly detected heart beat, data may be stored in the rolling buffer indicating a timing of that heart beat, as described herein and with regards to FIG. 6.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. Methods and processes disclosed herein may be performed by hardware or software implemented on a client device or on a remote device such as a server or datacenter or other cloud-based, remote resource. FIGS. 1A and 1B show one, non-limiting example of a sensory-and-logic system to enact the methods and processes described herein. These methods and process may also be enacted on sensory-and-logic systems of other configurations and form factors, as shown schematically in FIG. 8.

Figure 8:
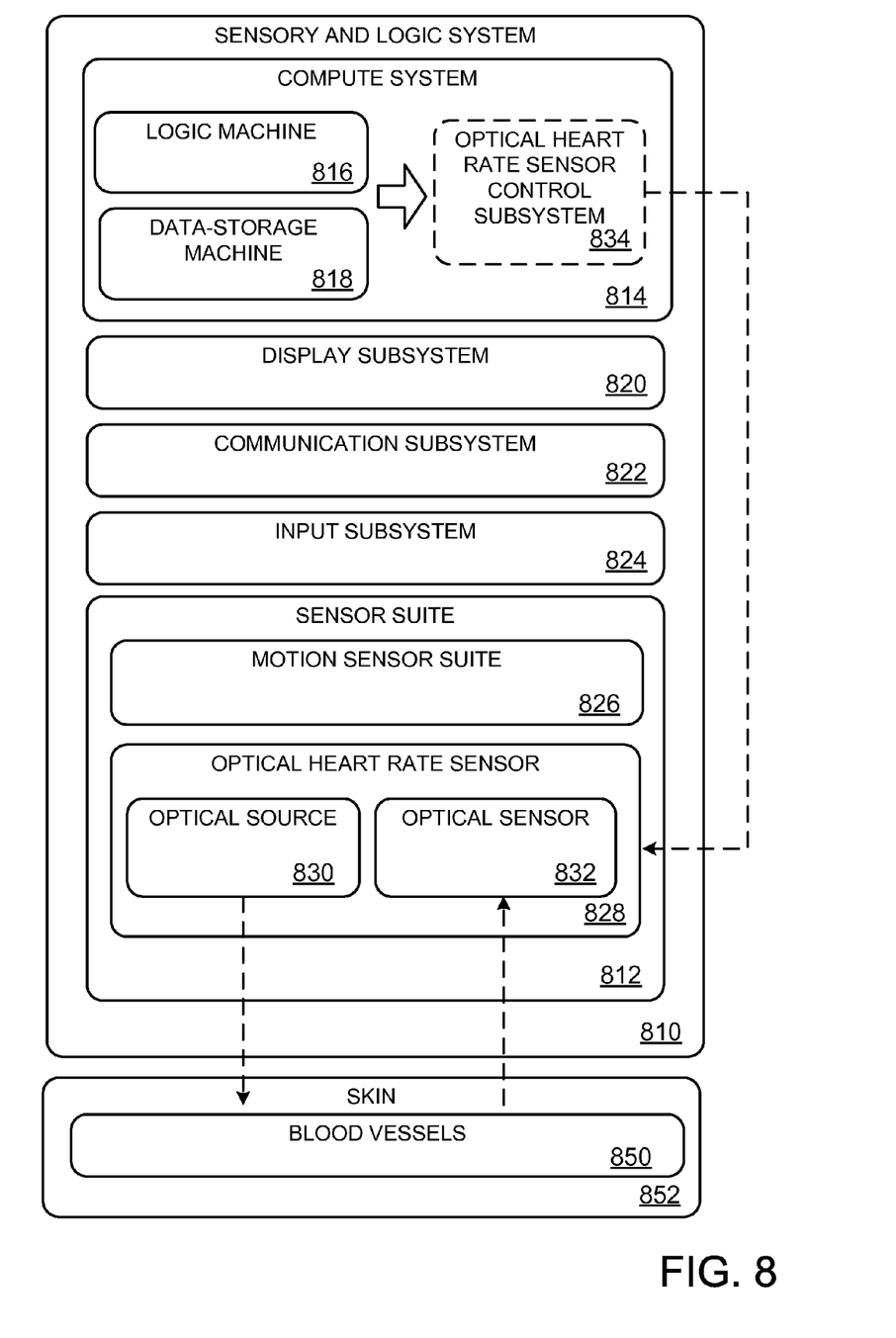
FIG. 8 schematically shows a sensory and logic system useable to monitor signal quality of an optical heart rate sensor.

FIG. 8 schematically shows a form-agnostic sensory-and-logic system 810 that includes a sensor suite 812 operatively coupled to a compute system 814. The compute system includes a logic machine 816 and a data-storage machine 818. The compute system is operatively coupled to a display subsystem 820, a communication subsystem 822, an input subsystem 824, and/or other components not shown in FIG. 8.

Logic machine 816 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 816 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 818 includes one or more physical devices configured to hold instructions executable by logic machine 816 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

It will be appreciated that data-storage machine 818 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 816 and data-storage machine 818 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 820 may be used to present a visual representation of data held by data-storage machine 818. This visual representation may take the form of a graphical user interface (GUI). As the herein described methods and processes change the data held by the storage machine, and thus transform the state of the storage machine, the state of display subsystem 820 may likewise be transformed to visually represent changes in the underlying data. Display subsystem 820 may include one or more display subsystem devices utilizing virtually any type of technology. Such display subsystem devices may be combined with logic machine 816 and/or data-storage machine 818 in a shared enclosure, or such display subsystem devices may be peripheral display subsystem devices. Display 20 of FIGS. 1A and 1B is an example of display subsystem 820.

Communication subsystem 822 may be configured to communicatively couple compute system 814 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 822.

Input subsystem 824 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 824.

Sensor suite 812 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 812 may include motion sensor suite 826. Motion sensor suite 826 may include one or more of an accelerometer, gyroscope, magnetometer, or other suitable motion detectors. Sensor suite 812 may further include optical heart rate sensor 828. As described herein, optical heart rate sensor 828 may include optical source 830 and optical sensor 832. Compute system 814 may include optical heart rate control subsystem 834, which may be communicatively coupled to logic machine 816 and data-storage machine 818. Optical source 830 may comprise one or more LED emitters, for example, while optical sensor 832 may comprise one or more photodiodes matched to detect light at frequencies that are based on the frequencies of light output by the optical source. Optical source 830 may be configured to illuminate one or more blood vessels 850 through the skin 852 of the user, and optical sensor 832 may be configured to measure illumination reflected from or transmitted through blood vessels 850.

Optical heart rate control subsystem 834 may receive raw signals from optical sensor 832, and may further process the raw signals to determine heart rate, caloric expenditures, etc. Processed signals may be stored and output via compute system 814. Control signals sent to optical source 830 and optical sensor 832 may be based on signals received from optical sensor 832, signals derived from sensor suite 812, information stored in data-storage machine 818, input received from communication subsystem 822, input received from input subsystem 824, etc.

It will be understood that the configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A method for calculating a heart rate, comprising:
   receiving data indicating a timing of a plurality of detected heart beats;
   for each of the plurality of detected heart beats, storing data indicating the timing of each heart beat in a first-in-first-out rolling buffer;
   determining an average duration between each pair of consecutive heart beats represented by data currently stored in the rolling buffer;
   following the receipt of data indicating detection of one of a plurality of new heart beats, determining a duration between the newly detected heart beat and an immediately previously detected heart beat;
   comparing the duration between the newly detected heart beat and the immediately previously detected heart beat to the average duration between each pair of consecutive heart beats represented by data currently stored in the rolling buffer;
   adjusting the duration between the newly detected heart beat and the immediately previously detected heart beat so that the adjusted duration is closer to the average duration based on the duration between the newly detected heart beat and the immediately previously detected heart beat differing from the average duration by more than a duration threshold;

adding new data indicating an adjusted timing of the newly detected heart beat to the rolling buffer, the adjusted timing based on the adjusted duration;

responsive to determining that a number of data adjustments exceed a counting threshold within a predetermined time period, choosing a repopulation value from data stored within the rolling buffer representative of a most recent duration between consecutive heart beats that did not differ from the average duration by more than the duration threshold; and repopulating each slot of the rolling buffer with the repopulation value.

2. The method of claim 1, where adjusting the duration between the newly detected heart beat and the immediately previously detected heart beat so that the adjusted duration is closer to the average duration between each pair of consecutive heart beats stored in the rolling buffer comprises:

setting a stored duration value indicating a timing between the newly detected heart beat and the immediately previously detected heart beat equal to a sum of the average duration and the duration threshold if the duration between the newly detected heart beat and the immediately previously detected heart beat is greater than the sum of the average duration and the duration threshold; and setting a stored duration value indicating a timing between the newly detected heart beat and the immediately previously detected heart beat equal to a difference of the average duration and the duration threshold if the duration between the newly detected heart beat and the immediately previously detected heart beat is less than the difference of the average duration and the duration threshold.

3. The method of claim 1, where the duration threshold is based on a percentage of the average duration between each pair of consecutive heart beats stored in the rolling buffer.

4. The method of claim 1, where data indicating a timing of each detected heart beat comprises a timing of a zero-crossing event based on a received signal from an optical heart rate sensor.

5. The method of claim 4, where a timing of each zero-crossing event is based on a timing of a light pulsation from an optical source of the optical heart rate sensor.

6. The method of claim 1, further comprising:
following repopulating the rolling buffer, discarding newly received data representing a predetermined number of heart beats without adding the newly received data to the rolling buffer; and then adding data representing subsequent newly detected heart beats to the rolling buffer.

7. A method for calculating a heart rate, comprising:
detecting a plurality of heart beats based on a measured intensity of light over time;
for each detected heart beat, storing data indicating a timing of that heart beat in a first-in-first-out rolling buffer;
responsive to determining that the measured intensity of light changes with a frequency greater than a threshold during a first predetermined time period,
determining an average duration between each pair of consecutive detected heart beats within a second predetermined time period, at least in part by:

determining a duration between each pair of consecutive detected heart beats over the second predetermined time period;
comparing each determined duration to a threshold; and
determining the average duration based only on determined durations having values below the threshold;
clearing the rolling buffer; and
repopulating each slot of a first segment of the rolling buffer, the first segment including two or more slots, with a value equal to the average duration between each pair of consecutive detected heart beats within the second predetermined time period.

8. The method of claim 7, where detecting a heart beat further comprises:
illuminating one or more blood vessels through a user's skin with an optical source; and
measuring reflected illumination from the one or more blood vessels with an optical sensor.

9. The method of claim 7, further comprising:
determining an average duration between newly detected heart beats over one or more additional predetermined time periods based on a measured intensity of light over the additional predetermined time periods, the additional predetermined time periods being equal in duration to the second predetermined time period;
repopulating one or more additional segments of the rolling buffer with a value equal to the average duration between newly detected heart beats over a corresponding predetermined time period until the rolling buffer is filled; and then
for each newly detected heart beat, storing data indicating a timing of the newly detected heart beat in the rolling buffer.

10. The method of claim 9, further comprising:
storing a first-in-first-out motion buffer of data indicating detected movement based on signals received from one or more motion sensors; and
filtering a signal from an optical sensor based on the data stored within the motion buffer prior to detecting a heart beat based on the signal from the optical sensor.

11. The method of claim 10, further comprising:
clearing the motion buffer concurrent to clearing the rolling buffer; and
repopulating a first segment of the motion buffer based on signals received from the one or more motion sensors over the second predetermined time period.

12. An optical heart rate system, comprising:
an optical source configured to illuminate one or more blood vessels through a user's skin;
an optical sensor configured to measure illumination reflected off the one or more blood vessels; and
a storage machine holding instructions executable by a logic machine to:
receive a signal from the optical sensor indicating a measured intensity of light over time;
detect a plurality of heart beats based on the signal received from the optical sensor;
for each detected heart beat, store data indicating a timing of that heart beat in a first-in-first-out rolling buffer;
during a first condition:
generating data indicating a timing of a newly detected heart beat relative to an immediately previously detected heart beat based on the signal received from the optical sensor;
adjusting the generated data such that the indicated timing between the newly detected heart beat and the immediately previously detected heart beat is closer to an average duration between each pair of consecutive heart beats stored in the rolling buffer if the duration between the newly detected heart beat and the immediately previously detected heart beat differs from the average duration by more than a duration threshold;

storing the adjusted generated data in the rolling buffer; and responsive to determining that a number of data adjustments exceed a counting threshold within a predetermined time period, choosing a repopulation value from data stored within the rolling buffer representative of a most recent duration between consecutive heart beats that did not differ from the average duration by more than the duration threshold; and repopulating each slot of the rolling buffer with the repopulation value; and during a second condition:

responsive to determining that the measured intensity of light changes with a frequency greater than a threshold over a first predetermined time period, determine an average duration between newly detected heart beats over a second predetermined time period based on a measured intensity of light over the second predetermined time period; and repopulate a first segment of the rolling buffer with a value equal to the average duration between newly detected heart beats over the second predetermined time period.

13. The optical heart rate system of claim 12, where the storage machine further holds instructions executable by the logic machine to:

during the first condition:

set a stored value indicating the duration between the newly detected heart beat and the immediately previously detected heart beat equal to a sum of the average duration and the duration threshold if the duration between the newly detected heart beat and the immediately previously detected heart beat is greater than the sum of the average duration and the duration threshold; and set a stored value indicating the duration between the newly detected heart beat and the immediately previously detected heart rate equal to a difference of the average duration and the duration threshold if the duration between the newly detected heart beat and the immediately previously detected heart rate is less than the difference of the average duration and the duration threshold.

14. The optical heart rate system of claim 13, where the storage machine further holds instructions executable by the logic machine to:

during the first condition:

following repopulating the rolling buffer, discard a predetermined number of newly detected heart beats prior to adding newly detected heart beats to the rolling buffer.

15. The optical heart rate system of claim 12, where the storage machine further holds instructions executable by the logic machine to:

during the second condition:

determine an average duration between newly detected heart beats over one or more additional predetermined time periods based on a measured intensity of light over the additional predetermined time periods, the additional predetermined time periods being equal in duration to the second predetermined time period;

repopulate each slot of one or more additional segments of the rolling buffer with a value equal to the average duration between newly detected heart beats over a corresponding predetermined time period until the rolling buffer is filled; and then for each newly detected heart beat, store data indicating a timing of that heart beat in the rolling buffer.

16. The optical heart rate system of claim 12, further comprising:

one or more motion sensors; and where the storage machine further holds instructions executable by the logic machine to:

store a rolling motion buffer of data indicating detected movement based on signals received from one or more motion sensors; and filter a signal from an optical sensor based on the data stored within the rolling motion buffer prior to detecting a heart beat based on the signal from the optical sensor.

17. The optical heart rate system of claim 12, where data indicating a timing of a detected heart beat comprises a timing of a zero-crossing event based on a received signal from the optical sensor.

18. The optical heart rate system of claim 17, where the optical source is configured to pulse on and off at a pulsation frequency.

19. The optical heart rate system of claim 18, where the timing of a zero-crossing event is based on a timing of a light pulsation from the optical source.

* * * * *